US00PP18518P2

(12) United States Plant Patent
Li

(10) Patent No.: US PP18,518 P2
(45) Date of Patent: Feb. 26, 2008

(54) ***VERBENA* PLANT NAMED 'KLEVP05339'**

(50) Latin Name: *Verbena hybrida*
Varietal Denomination: KLEVP05339

(75) Inventor: Ruijun Li, North Parramata (AU)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/583,602

(22) Filed: Oct. 19, 2006

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Verbena* plant named 'KLEVEP0539', characterized by its mounding to cascading and compact plant habit; freely branching habit; freely flowering habit; light red purple-colored flowers that are held above and beyond the foliage; and resistance to Powdery Mildew.

1 Drawing Sheet

Botanical designation: *Verbena hybrida.*
Cultivar denomination: 'KLEVP05339'.

BACKGROUND OF THE INVENTION

The present invention relates to a new and distinct cultivar of *Verbena,* botanically known as *Verbena hybrida,* and hereinafter referred to by the name 'KLEVEP05339'.

The new *Verbena* is a product of a planned breeding program conducted by the Inventor in Camden, New South Wales, Australia. The objective of the breeding program is to create new disease-resistant *Verbena* cultivars with compact plant habit and attractive flower coloration.

The new *Verbena* originated from a cross-pollination made by the Inventor in 2002 in Camden, New South Wales, Australia of a proprietary seedling selection of *Verbena hybrida* identified as code number 00.520.1, not patented, as the female, or seed, parent with a proprietary seedling selection of *Verbena hybrida* identified as code number 00.28.1, not patented, as the male, or pollen, parent. The new *Verbena* was discovered and selected by the Inventor as a single flowering plant within the progeny of the stated cross-pollination in a controlled environment in Camden, New South Wales, Australia in 2002.

Asexual reproduction of the new *Verbena* by terminal cuttings in a controlled environment in Stuttgart, Germany since 2002 has shown that the unique features of this new *Verbena* are stable and reproduced true to type in successive generations.

SUMMARY OF THE INVENTION

The cultivar KLEVEP05339 has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'KLEVEP05339'. These characteristics in combination distinguish 'KLEVEP05339' as a new and distinct cultivar of *Verbena:*

1. Mounding to cascading and compact plant habit.
2. Freely branching habit.
3. Freely flowering habit.
4. Light red purple-colored flowers that are held above and beyond the foliage.
5. Resistant to Powdery Mildew.

Plants of the new *Verbena* can be compared to plants of the female parent selection. Plants of the new *Verbena* differ from plants of the female parent selection in the following characteristics:

1. Plants of the new *Verbena* are more mounding and cascading than plants of the female parent selection.
2. Plants of the new *Verbena* and the female parent selection differ in flower color as plants of the female parent selection have purple-colored flowers.

Plants of the new *Verbena* can be compared to plants of the male parent selection. Plants of the new *Verbena* differ from plants of the male parent selection in the following characteristics:

1. Plants of the new *Verbena* are more mounding and cascading than plants of the male parent selection.
2. Plants of the new *Verbena* and the male parent selection differ in flower color as plants of the male parent selection have red-colored flowers.

Plants of the new *Verbena* can be compared to plants of the *Verbena* cultivar V 315, not patented. In side-by-side comparisons conducted in Stuttgart, Germany, plants of the new *Verbena* differed from plants of the cultivar V 315 in the following characteristics:

1. Plants of the new *Verbena* were more compact than plants of the cultivar V 315.
2. Plants of the new *Verbena* were more freely branching than plants of the cultivar V 315.
3. Plants of the new *Verbena* had smaller leaves than plants of the cultivar V 315.
4. Plants of the new *Verbena* were more resistant to Powdery Mildew than plants of the cultivar V 315.

BRIEF DESCRIPTION OF THE PHOTOGRAPH

The accompanying colored photograph illustrates the overall appearance of the new *Verbena,* showing the colors as true as it is reasonably possible to obtain in colored reproductions of this type. Colors in the photograph may differ slightly from the color values cited in the detailed botanical description which accurately describe the colors of the new *Verbena.* The photograph comprises a side perspective view of a typical flowering plant of 'KLEVEP05339' grown in a container.

DETAILED BOTANICAL DESCRIPTION

The photograph and following observations, measurements and values describe plants grown in Stuttgart, Germany in a glass-covered greenhouse during the spring and summer and under conditions which closely approximate commercial production. During the production of the plants, day temperatures ranged from 18° C. to 22° C., night temperatures ranged from 15° C. to 18° C. and maximum light levels ranged from 20,000 lux to 55,000 lux. Plants were pinched one time and were about five months old when the photograph and the description were taken. In the description, color references are made to The Royal Horticultural Society Colour Chart, 1995 Edition, except where general terms of ordinary dictionary significance are used.

Botanical classification: *Verbena hybrida* cultivar KLEVEP05339.

Parentage:

*Female, or seed, parent.*—Proprietary seedling selection of *Verbena hybrida* identified as code number 00.520.1, not patented.

*Male, or pollen, parent.*—Proprietary seedling selection of *Verbena hybrida* identified as code number 00.28.1, not patented.

Propagation:

*Type.*—Terminal cuttings.

*Time to initiate roots, summer.*—About 14 days at 20° C. to 22° C.

*Time to initiate roots, winter.*—About 20 days at 20° C. to 22° C.

*Time to produce a rooted cutting, summer.*—About 60 days at 20° C. to 22° C.

*Time to produce a rooted cutting, winter.*—About 70 days at 20° C. to 22° C.

*Root description.*—Fine, fibrous; pale white in color.

*Rooting habit.*—Moderate branching; moderately dense.

Plant description:

*Plant habit.*—Initially upright, then mounding to cascading plant habit; compact growth habit. Freely branching habit with about five primary lateral branches per plant each with numerous secondary branches; pinching enhances lateral branch development; dense and bushy plant habit. Moderately vigorous growth habit.

*Plant height.*—About 5 cm.

*Plant diameter.*—About 35 cm.

Lateral branch description:

*Length.*—About 20 cm.

*Diameter.*—About 2.5 mm.

*Internode length.*—About 3 cm to 5 cm.

*Strength.*—Weak.

*Texture.*—Pubescent.

*Color.*—141D.

Foliage description:

*Arrangement.*—Opposite, simple.

*Length.*—About 3 cm.

*Width.*—About 3 cm.

*Shape.*—Deeply dissected.

*Apex.*—Cuspidate.

*Base.*—Obtuse.

*Margin.*—Deeply dissected.

*Texture, upper and lower surfaces.*—Smooth, glabrous.

*Venation pattern.*—Pinnate.

*Color.*—Developing foliage, upper and lower surfaces: 141C. Fully expanded foliage, upper and lower surfaces: 141C; venation, 141C.

*Petiole.*—Length: About 2 cm. Diameter: About 0.2 mm. Texture, upper and lower surfaces: Smooth, glabrous. Color, upper and lower surfaces: 68D.

Flower description:

*Flower arrangement and habit.*—Salverform flowers arranged in hemispherical terminal umbels; flowers face upward or outward. Freely flowering habit with about 20 flowers per inflorescence.

*Natural flowering season.*—Plants flower continuously from the spring through the fall in Germany.

*Flower longevity.*—Flowers last about two weeks on the plant. Flowers not persistent.

*Fragrance.*—None detected.

*Flowers.*—Appearance: Flared trumpet, corolla fused, five-parted. Diameter: About 2 cm. Depth (height): About 2 cm. Tube length: About 2 cm. Throat diameter: About 1 mm. Tube diameter, base: About 0.5 mm.

*Flower buds.*—Length: About 2 cm. Diameter: About 3 mm. Shape: Elongate, oblong. Color: 68D.

*Corolla.*—Arrangement: Single whorl of five fused petals. Petal lobe length: About 1 cm. Petal lobe width: About 1 cm. Petal lobe shape: Roughly cordate. Petal lobe apex: Emarginate to cordate. Petal margin: Entire. Petal texture, upper and lower surfaces: Smooth, glabrous. Color: Petal, when opening, upper surface: 68A. Petal, when opening, lower surface: 68B. Petal, fully opened, upper surface: 68B; color becoming closer to 68C with development. Petal, fully opened, lower surface: 68C. Throat: 65D. Tube: 68C.

*Calyx.*—Arrangement: One single narrow calyx tube per flower with five fused sepals. Sepal length: About 1.5 cm. Sepal width: About 2 mm. Sepal shape: Lanceolate. Sepal apex: Acute. Sepal base: Obtuse. Sepal margin: Serrate. Sepal texture, upper and lower surfaces: Pubescent; rough. Sepal color, upper surface: 67D. Sepal color, lower surface: 68D.

*Peduncles.*—Length: About 1.5 cm. Diameter: About 0.1 mm. Strength: Moderately strong. Texture: Pubescent; rough. Color: 141C.

*Pedicels.*—Flowers are sessile.

*Reproductive organs.*—Stamens: Quantity/arrangement: Four per flower, adnate to corolla tube. Anther shape: Elliptic. Anther length: Less than 1 mm. Anther color: 142D. Pollen amount: None observed. Pistils: Minute. Quantity: One per flower. Stigma shape: Lanceolate. Stigma color: 142D. Style color: 142D. Ovary color: 142D. Fruits/seed: Fruit and seed development have not been observed.

Temperature tolerance: Plants of the new *Verbena* have been observed to tolerate temperatures from about 1° C. to about 40° C.

Pathogen/pest resistance: Plants of the new *Verbena* have been observed to be resistant to Powdery Mildew. Plants of the new *Verbena* have not been observed to be resistant to pests and other pathogens common to *Verbenas*.

It is claimed:

1. A new and distinct *Verbena* plant named 'KLEVEP05339' as illustrated and described.

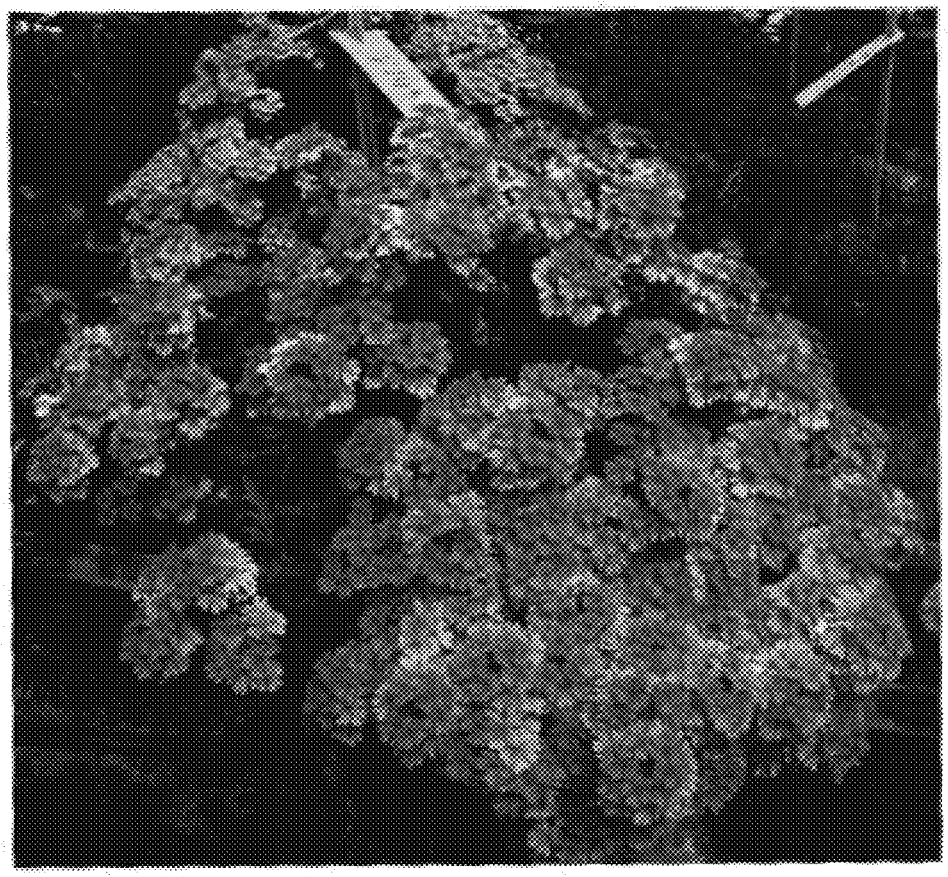

* * * * *